United States Patent
Seo et al.

(10) Patent No.: US 8,778,322 B2
(45) Date of Patent: *Jul. 15, 2014

(54) PH RESPONSIVE BIODEGRADABLE POLYLACTIC ACID DERIVATIVES FORMING POLYMERIC MICELLES AND USES THEREOF FOR POORLY WATER SOLUBLE DRUG DELIVERY

(75) Inventors: Min-Hyo Seo, Daejeon (KR); Bong-Oh Kim, Daejeon (KR); In-Ja Choi, Daejeon (KR); Myung-Seob Shim, Seoul (KR)

(73) Assignee: Samyang Biopharmaceuticals Corporation, Seoul (KR)

( * ) Notice: Subject to any disclaimer, the term of this patent is extended or adjusted under 35 U.S.C. 154(b) by 2073 days.

This patent is subject to a terminal disclaimer.

(21) Appl. No.: 10/492,091

(22) PCT Filed: Oct. 17, 2002

(86) PCT No.: PCT/KR02/01943
§ 371 (c)(1),
(2), (4) Date: Apr. 9, 2004

(87) PCT Pub. No.: WO03/033593
PCT Pub. Date: Apr. 24, 2003

(65) Prior Publication Data
US 2004/0247561 A1 Dec. 9, 2004

(30) Foreign Application Priority Data
Oct. 18, 2001 (KR) ........................ 10-2001-0064164

(51) Int. Cl.
*A61K 31/74* (2006.01)
*C08G 63/08* (2006.01)

(52) U.S. Cl.
USPC ........................................ 424/78.08; 525/450

(58) Field of Classification Search
USPC .................. 424/78.27, 70.11, 78.08; 525/450
See application file for complete search history.

(56) References Cited

U.S. PATENT DOCUMENTS

| 4,010,196 A | * | 3/1977 | Tsuk | 560/185 |
| 4,479,911 A | | 10/1984 | Fong | |
| 5,665,428 A | * | 9/1997 | Cha et al. | 427/213.3 |
| 6,447,796 B1 | * | 9/2002 | Vook et al. | 424/422 |
| 8,021,652 B2 | * | 9/2011 | Seo et al. | 424/78.37 |

FOREIGN PATENT DOCUMENTS

| EP | 0 330 180 | * | 8/1989 |
| EP | 0 728 862 A2 | * | 8/1996 |
| EP | 0330180 A1 | | 8/1998 |

OTHER PUBLICATIONS

Zhang et al. ("Effects of metal salts on poly (DL-lactide-co-glycolide) polymer hydrolysis," in Journal of Biomedical Materials Research, vol. 34, 531-538 (1997).*
Jones et al., "Polymeric micelles—a new generation of colloidal drug carriers," in European Journal of Pharmaceutics and Biopharmaceutics, 48, (1999), 101-111).*

* cited by examiner

*Primary Examiner* — Blessing M Fubara
(74) *Attorney, Agent, or Firm* — Birch, Stewart, Kolasch & Birch, LLP

(57) ABSTRACT

Polylactic acid derivatives capable of forming micelles in an aqueous solution with a pH of 4 or above, having one terminal carboxyl group. The polylactic acid derivatives may be applied as a drug delivery system in various forms since poorly water soluble drugs can be entrapped inside the micelles.

22 Claims, 7 Drawing Sheets a: $^1$H-NMR peak for hydrogen "a" indicated in the following formula
b: $^1$H-NMR peak for hydrogen "b" indicated in the following formula
c: $^1$H-NMR peak for hydrogen "c" indicated in the following formula a: ¹H-NMR peak for hydrogen "a" indicated in the following formula
b: ¹H-NMR peak for hydrogen "b" indicated in the following formula
c: ¹H-NMR peak for hydrogen "c" indicated in the following formula
d: ¹H-NMR peak for hydrogen "d" indicated in the following formula (a): Peak showing the sodium salt of a D,L-polylactic acid that forms micelles
(b): Peak showing the sodium salt of a D,L-polylactic acid that does not form micelles

PH RESPONSIVE BIODEGRADABLE POLYLACTIC ACID DERIVATIVES FORMING POLYMERIC MICELLES AND USES THEREOF FOR POORLY WATER SOLUBLE DRUG DELIVERY

TECHNICAL FIELD

The present invention relates to polylactic acid derivatives capable of forming micelles in an aqueous solution with a pH of 4 or above and having one terminal carboxyl group, and more specifically, to a polymeric micelle composition comprising the polylactic acid derivatives.

BACKGROUND OF THE INVENTION

Solubilization of poorly water soluble drugs is essential for the delivery of the drugs by oral or parenteral administration. There are several conventional methods for solubilization of poorly water soluble drugs. For example, a poorly water soluble drug may be dissolved in a mixture of a water-miscible organic solvent and water. Alternatively, structural modification of a poorly water soluble drug from its acid or base to its salt form may increase the water solubility of the drug. Other methods include complexation of a poorly water soluble drug with a third substance or entrapment of a poorly water soluble drug into micelles formed by a surfactant. See Leon Lachman, "*The theory and practice of industrial pharmacy*", Lea & Febiger, Philadelphia, 1986.

Among the above methods, the micelles formed by use of a surfactant may be manufactured to have a size of several nm to several μm, and may be finely dispersed in an aqueous solution. Therefore, use of micelles has been preferred for the solubilization of poorly water soluble drugs.

Surfactants have a chemical structure comprising a hydrophilic block and a hydrophobic block, wherein the hydrophilic block has high affinity for water on one side and the hydrophobic block, has a high affinity for oil on the other side. If the hydrophilic block is dominant, the surfactants dissolve better in water, and conversely, if the hydrophobic block is dominant, the surfactants dissolve better in an organic solvent. Surfactants are classified into ionic and non-ionic. In the method of solubilization for a poorly water soluble drug, the non-ionic surfactant does not affect the poorly water soluble drug through ionic interactions due to its electronic neutrality. Such surfactants include anion salts of fatty acid derivatives, sorbitan derivatives such as Tween or Span, polyoxyethylene monoalkylether derivatives (BRIJ and MYRJ series) and polyethylene glycol ester derivatives of fatty acids, polyoxyethylated caster oil derivatives such as Cremophor, etc., and the like.

EP 0,645,145 discloses a method in which paclitaxel, a poorly water soluble drug, is solubilized using Cremophor EL which is a non-ionic surfactant. However, the drug solubilized by the surfactant has limited use due to adverse side effects, such as hypersensitive reactions, when it is administered orally or parentally. It also has the drawback in that the drug is separated from the micelles when stored for a long time since the stability of the micelles in an aqueous solution is very low.

Use of a polymeric micelle made of a di- or tri-block copolymer comprising a hydrophilic polymer of polyalkylene glycol derivatives and a hydrophobic biodegradable polymer such as fatty acid polyesters or polyamino acids for solubilization of a hydrophobic drug has been reported. For example, U.S. Pat. No. 5,449,513 discloses a diblock copolymer comprising a polyethylene glycol as the hydrophilic polymer, and a polyamino acid derivative, e.g. polybenzyl aspartic acid, etc., as the hydrophobic polymer. The diblock copolymer can solubilize hydrophobic anticancer agents, e.g. doxorubicin, or anti-inflammatory agents, e.g. indomethacin. However, the drawback is that the polyamino acid derivative is not hydrolyzed in vivo and causes undesired side effects.

Furthermore, U.S. Pat. No. 5,429,826 discloses a di- or multi-block copolymer comprising a hydrophilic polyalkylene glycol and a hydrophobic polylactic acid. Specifically, the above patent describes a method for stabilization of a polymeric micelle by micellizing a di- or multi-block copolymer having an acrylic acid terminal group in an aqueous solution, and then, crosslinking the micelle. Although this method may improve the stability of the polymeric micelles, the drawback is that the crosslinked polymer is not degraded, and thus, cannot be applied for in vivo use.

Polylactic acid has been applied for drug delivery systems in various forms because it has an excellent biocompatibility and biodegradability. Polylactic acids have various properties depending on their molecular weight, and have been developed in various formulations such as microspheres, nanoparticles, polymeric gels, implant agents, and the like. However, polylactic acids having a molecular weight of more than 2,000 Daltons are not dissolvable in aqueous solutions. There has been no reported success in developing polylactic acids having molecular weights of less than 2,000 Daltons as drug delivery systems since they are not dissolvable in an aqueous solution of a pH of 4 or more.

In view of the foregoing, development of an improved polymeric micelle composition for hydrophobic drug delivery, that is biocompatible and biodegradable, will be appreciated and desired. The present invention provides for such an improved polymeric micelle composition, which is biocompatible and biodegradable, and which can effectively deliver a hydrophobic drug without a decrease in its stability.

BRIEF SUMMARY OF THE INVENTION

The present invention relates to polylactic acid derivatives capable of forming micelles in an aqueous solution with a pH of 4 or more and which can entrap a poorly water soluble drug inside the above micelles, whereby the poorly water soluble drug can be solubilized. More specifically, the polylactic acid derivatives of the present invention have molecular weights of 500 to 2,000 Daltons and can be prepared by polycondensing 2-hydroxy carboxylic acid derivatives.

The present invention further provides a preparation method for polylactic acid derivatives which are obtained by polycondensing 2-hydroxy carboxylic acid derivatives at elevated temperatures while under reduced pressure without the presence of a catalyst.

The present invention still further provides a polymeric composition comprising micelles formed by the polylactic acid derivatives.

The present invention still further provides a pharmaceutical composition in which a poorly water soluble drug is entrapped in the micelles that are formed by polylactic acid derivatives, at a pH 4 or more.

The polylactic acid derivatives of the present invention can be represented by formula (I)

$$\text{RO--CHZ-[A]}_n\text{-[B]}_m\text{-COOM} \tag{I}$$

wherein A is —COO—CHZ; B is —COO—CHY—, —COO—CH$_2$CH$_2$CH$_2$CH$_2$CH$_2$—, or —COO—CH$_2$CH$_2$OCH$_2$—; R is a hydrogen, acetyl, benzoyl, decanoyl, palmitoyl, methyl, or ethyl group; Z and Y are hydrogen, methyl, or phenyl groups; M is hydrogen, sodium, potassium, or lithium; n is an integer from 1 to 30, and m is an integer from 0 to 20.

The polylactic acid derivatives of the present invention can form micelles in an aqueous solution of pH 4 or more. The formed micelles have sizes of 10 to 21 nm, and so are suitable to be carriers of a poorly water-soluble drugs. Hereinafter, the present invention will be explained in more detail.

BRIEF DESCRIPTION OF DRAWINGS

In FIG. 3, (a) is a peak showing the sodium salt of a D,L-polylactic acid that forms micelles, and (b) is a peak showing the sodium salt of a D,L-polylactic acid that does not form micelles.

DETAILED DESCRIPTION

Figure 1:
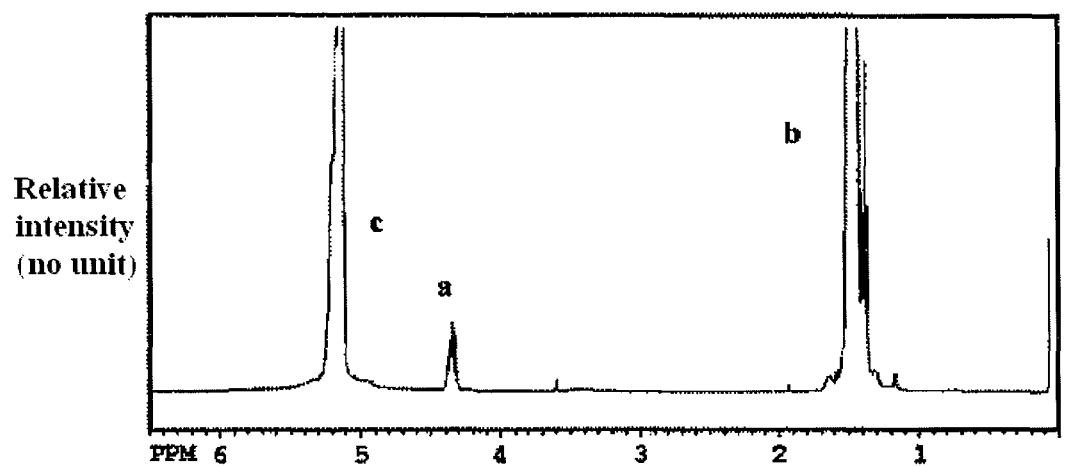
FIG. 1 is a graph showing an $^1$H-NMR spectrum of a D,L-polylactic acid of the present invention.
Figure 1:
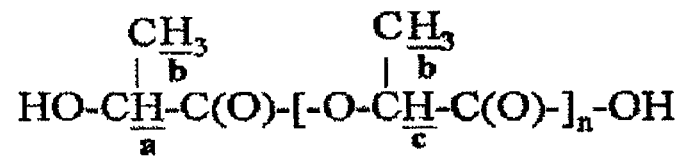

Before the present polymeric compositions and methods of use and making thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a polymer containing "a terminal group includes reference to two or more such groups, and reference to "a hydrophobic drug" includes reference to two or more of such drugs.

In describing and claiming the present invention, the following terminology will be used in accordance with the definitions set out below.

As used herein, the term "bioactive agent" or "drug" or any other similar term means any chemical or biological material or compound suitable for administration by methods previously known in the art and/or by the methods taught in the present invention and that induce a desired biological or pharmacological effect. Such effects may include but are not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating a disease from the organism. The effect may be local, such as providing for a local anesthetic effect, or it may be systemic.

As used herein, the term "biodegradable" or "biodegradation" is defined as the conversion of materials into less complex intermediates or end products by solubilization hydrolysis, or by the action of biologically formed entities which can be enzymes or other products of the organism.

As used herein, the term "biocompatible" means materials or the intermediates or end products of materials formed by solubilization hydrolysis, or by the action of biologically formed entities which can be enzymes or other products of the organism and which cause no adverse effects on the body.

"Poly(lactide)" or "PLA" shall mean a polymer derived from the condensation of lactic acid or by the ring opening polymerization of lactide. "Poly(glycolide)" or "PGA" shall mean a polymer derived from the condensation of glycolic acid or by the ring opening polymerization of glycolide. As used herein, "effective amount" means the amount of a bioactive agent that is sufficient to provide the desired local or systemic effect and performance at a reasonable risk/benefit ratio as would attend any medical treatment.

As used herein, "administering" and similar terms means delivering the composition to the individual being treated such that the composition is capable of being circulated systemically. Preferably, the compositions of the present invention are administered by the subcutaneous, intramuscular, transdermal, oral, transmucosal, intravenous, or intraperitoneal routes. Injectables for such use can be prepared in conventional forms, either as a liquid solution or suspension, or in a solid form that is suitable for preparation as a solution or suspension in a liquid prior to injection, or as an emulsion. Suitable excipients that can be used for administration include, for example, water, saline, dextrose, glycerol, ethanol, and the like; and if desired, minor amounts of auxiliary substances such as wetting or emulsifying agents, buffers, and the like. For oral administration, it can be formulated into various forms such as solutions, tablets, capsules, etc.

Reference will now be made to the exemplary embodiments and specific language will be used herein to describe the same. It will nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention.

The present invention relates to polylactic acid derivatives capable of forming micelles in an aqueous solution with a pH of 4 or more and which entrap a poorly water soluble drug inside the above micelles, thereby solubilizing the poorly water soluble drug. More particularly, the present invention relates to polylactic acid derivatives as shown in formula (I):

$$RO\text{---}CHZ\text{-}[A]_n\text{-}[B]_m\text{-}COOM \qquad (I)$$

wherein A is —COO—CHZ; B is —COO—CHY—, —COO—$CH_2CH_2CH_2CH_2CH_2$—, or —COO—$CH_2CH_2OCH_2$—; R is a hydrogen, acetyl, benzoyl, decanoyl, palmitoyl, methyl, or ethyl group; Z and Y are hydrogen, methyl, or phenyl groups; M is hydrogen, sodium, potassium, or lithium; n is an integer from 1 to 30, and m is an integer from 0 to 20.

The polylactic acid derivatives, as shown in formula (I), are preferably single polymers or random copolymers of 2-hydroxy carboxylic acid derivatives. More preferably, the polylactic acid derivative is a member selected from the group consisting of D,L-polylactic acids, copolymers of D,L-lactic acid and mandelic acid, copolymers of D,L-lactic acid and glycolic acid, copolymers of D,L-lactic acid and caprolactone, and copolymers of D,L-lactic acid and 1,4-dioxane-2-one.

One end of the polylactic acid derivatives of the present invention may be a carboxyl group or alkali metal salt thereof, preferably, an alkali metal salt. The alkali metal salt forms a polylactic acid derivative in the form of metal ion salt when the metal ion is monovalent, e.g. sodium, potassium or lithium. The polylactic acid derivatives of the present invention are solid at room temperature and are very stable at the exposure to moisture in the air because of its neutral pH.

The other end of the polylactic acid derivatives may be a hydroxyl group, may be esterified with a member selected from the group consisting of acetyl, benzoyl, decanoyl, palmitoyl and the like, or may be alkylated with a methyl, ethyl or an equivalent group thereof.

The polylactic acid derivatives of the present invention can be dissolved in aqueous solutions, wherein the hydrophilic and hydrophobic components of the polylactic acid derivatives are balanced to form polymeric micelles. Therefore, if the hydrophobic ester moiety has too large a molecular weight, the terminal carboxyl anionic groups cannot join, and thus, it is difficult to form the micelles. The number average molecular weights of the polylactic acid derivatives of the present invention are preferably within the range of 500 to 2,000 Daltons. If the molecular weight is less than 500, the polymer is completely dissolved in water, and thus, the micelles cannot be formed, and if the molecular weight is more than 2,000, the hydrophobicity is too strong to form micelles. The molecular weight of the polylactic acid derivatives can be adjusted by controlling the reaction temperature, vacuum, time, and the like during the preparation process.

Figure 7:
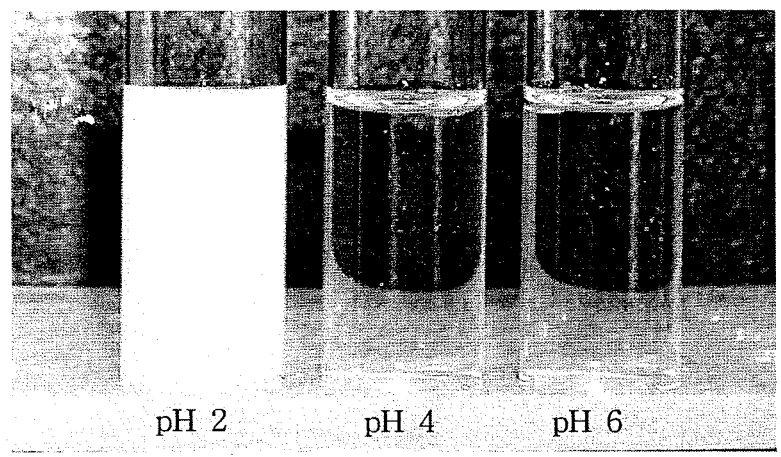
FIG. 7 is a graph showing the solubility of the sodium salt of a D,L-polylactic acid depending on the pH.

According to the following experiments of the present invention, the solubility of the polylactic acid derivatives of formula (I) varies depending on the pH of the environment. In an aqueous solution with a pH 4 or more, the polylactic acid derivatives of the present invention are completely dissolved resulting in a clear solution to the naked eye. However, if the pH of the solution is adjusted to be 4 or less, the polylactic acid derivatives are partially precipitated, as shown in FIG. 7. The polylactic acid derivatives, according to the present invention, may be used at a pH within the range of 1 to 10, and are preferably prepared and used at a pH within the range of 4 to 8.

Figure 3:
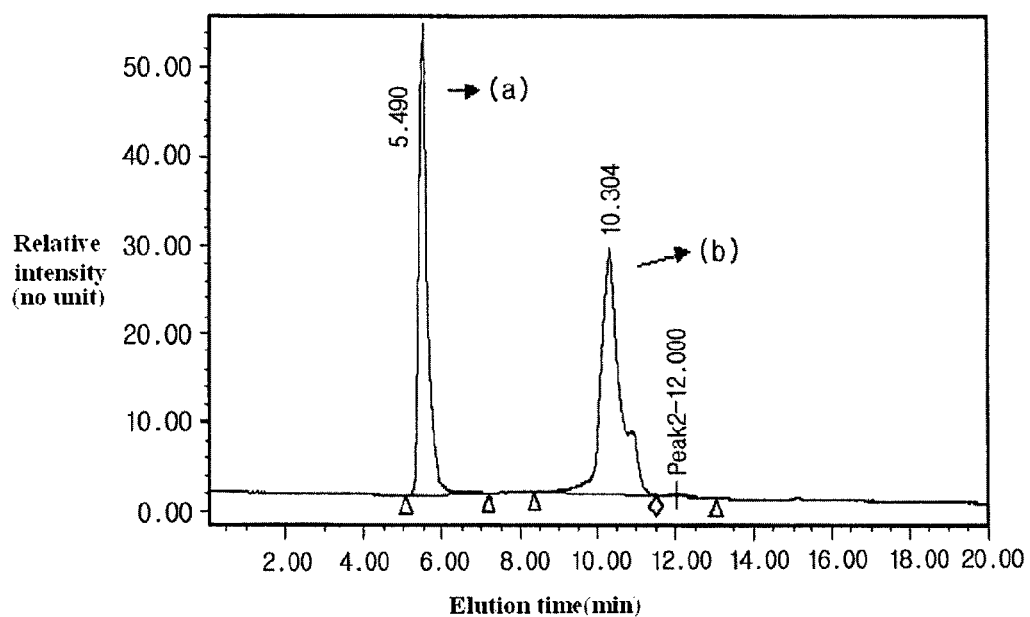
FIG. 3 is a graph showing the Size Exclusion Chromatography (SEC) spectrum of the sodium salt of a D,L-polylactic acid of the present invention.

The polylactic acid derivatives according to the present invention are dispersed in an aqueous solution with a pH of 4 or more and form micelles. The micelles formed can be identified by Size Exclusive Chromatography (SEC), and the sizes of the micelles are preferably in the range of about 9 to 21 nm. As shown in FIG. 3 and Table 6, it is demonstrated that the amount of micelles formed increases as the concentration of the polylactic acid derivative increases. It is also shown that the amount of micelles formed increases as the hydrophobicity of the terminal moiety is increased by substituting the hydroxyl terminal group with a decanoyl or palmitoyl group.

Another aspect of the present invention relates to a preparation method for polylactic acid derivatives as shown in formula (I). For example, the present invention provides a preparation method for polylactic acid derivatives as shown in formula (I) wherein R is a hydrogen, and a preparation method for the polylactic acid derivatives wherein R is an acetyl, benzoyl, decanoyl, palmitoyl, methyl, or ethyl group.

The preparation method for the polylactic acid derivatives of formula (I) wherein R is hydrogen comprises the steps of:

1) polycondensing the monomers of a polylactic acid derivative at an elevated temperature and under reduced pressure;

2) adding distilled water to the product of step 1) to precipitate the polylactic acid derivatives and thereby removing low-molecular weight oligomers;

3) adding the polylactic acid derivatives to a neutral or alkaline aqueous solution to dissolve the polylactic acid derivatives;

4) isolating the polylactic acid derivatives from the solution of step 3); and 5) adding an alkali metal salt to the polylactic acid derivatives obtained in step 4) to obtain the polylactic acid derivatives of formula (I) wherein R is hydrogen.

In the above method, step 5) may be omitted. When step 5 is omitted, a polylactic acid derivative that contains a carboxyl group unsubstituted by a metal ion at its terminus is formed.

More specifically, in step 1, the polylactic acid derivatives are obtained by polycondensing 2-hydroxy carboxylic acid derivatives, in the absence of a catalyst, at 100 to 200° C. under a reduced pressure of 25 to 0.1 mmHg, for 6 to 24 hours. As shown in the following Examples, the number average molecular weight and yield of the obtained polylactic acid derivatives vary depending on the temperature, condition of reduced pressure, and reaction time in step 1. By adjusting these conditions, the most preferable polylactic acid derivatives may be obtained. More specifically, the higher the reaction temperature is, the longer the reaction time goes, or the lower the reaction pressure is, the higher the number average molecular weight and the yields of the polylactic acid derivatives are.

In step 2, distilled water is added to the polylactic acid derivative, obtained in step 1, to precipitate the polylactic acid derivative and thereby remove the low-molecular weight oligomer that is soluble in water.

In step 3, the precipitated polylactic acid derivatives are dissolved in a neutral or alkaline aqueous solution having a pH of 7 or more, preferably a pH of 7 to 9.

In step 4, the polylactic acid derivatives are isolated by adjusting the pH of the aqueous solution in step 3 to 1.5-2.5 with 1N acid. Alternatively, to the aqueous solution of polylactic acid derivatives obtained in step 3 is added an organic solvent such as dichloromethane, chloroform, and the like, to extract the polylactic acid derivative, and the extracted polylactic acid derivatives are dried to obtain polylactic acid derivatives containing carboxyl terminal groups. The polylactic acid derivatives containing carboxyl terminal groups are preferably polymers having a number average molecular weight of 500 to 2,000 Daltons.

Furthermore, in step 5, the polylactic acid derivatives obtained in step 4 may be dissolved in acetone or an aqueous acetone solution. The resulting solution is then neutralized by adding an aqueous solution of sodium bicarbonate, sodium carbonate, potassium bicarbonate, potassium carbonate or lithium carbonate. The solvent is then evaporated resulting in the polylactic acid derivatives of formula (I) which are in the form of metal ion salts and wherein R is hydrogen.

The polylactic acid derivatives containing one terminal carboxyl group are viscous liquids at room temperature, and the polylactic acid derivatives containing a terminal carboxylate metal ion salt are solid at room temperature.

A preparation method for the polylactic acid derivatives of formula (I), wherein R is an acetyl, benzoyl, decanoyl, palmitoyl, methyl, or ethyl group, comprises the steps of:

1) polycondensing the monomers of a polylactic acid derivative at an elevated temperature and under reduced pressure;
2) adding distilled water to the product of step 1) to precipitate the polylactic acid derivative and thereby remove the low-molecular weight oligomer;
3) adding the polylactic acid derivative to a neutral or alkaline aqueous solution to dissolve the polylactic acid derivative;
4) isolating the polylactic acid derivative from the solution of step 3);
5) reacting the polylactic acid derivative obtained in step 4) with acetic anhydride, acetyl chloride, benzoyl chloride, decanoyl chloride, palmitoyl chloride, methyl iodide or ethyl iodide to substitute the hydroxyl terminal group; and
6) adding an alkali metal salt to the substituted polylactic acid derivative to obtain the polylactic acid derivative of formula (I) wherein R is an acetyl, benzoyl, decanoyl, palmitoyl, methyl, or ethyl group.

In the above method, step 6 may be omitted. When step 6 is omitted, a polylactic acid derivative that contains a carboxyl group unsubstituted by a metal ion at its terminus is formed.

In step 5, the polylactic acid derivatives containing carboxyl terminal groups are reacted with acetic anhydride, acetyl chloride, benzoyl chloride, decanoyl chloride, palmitoyl chloride, methyl iodide, or ethyl iodide to substitute the hydroxyl terminal group with esterified derivatives such as acetyl, benzoyl, decanoyl or palmitoyl groups, or alkylated derivatives such as methyl or ethyl groups.

The present invention also includes a polymeric composition comprising micelles formed by polylactic acid derivatives. The present invention also includes a pharmaceutical composition that contains a poorly water soluble drug entrapped in micelles farmed by polylactic acid derivatives at a pH of 4 or more.

For oral or parenteral administration of a poorly water-soluble drug, micelles comprising polylactic acid derivatives according to the present invention, are formed in an aqueous solution with a pH of 4 or more, and the poorly water soluble drug is entrapped within the micelle and is thus, solubilized. As shown in the following Examples, when the poorly water soluble drug is administered into the body, the micelles comprising the polylactic acid derivatives are disintegrated and thereby the poorly water soluble drug is slowly released and exhibits its pharmacological effects.

The poorly water soluble drug that can be solubilized, using the polylactic acid derivatives according to the present invention, is any drug as long as it has a water-solubility of 10 mg/ml or less. The typical poorly water soluble drugs include paclitaxel, ketoconazole, itraconazole, cyclosporine, cisapride, acetaminophen, aspirin, aceyl salicylic acid, indomethacin, naproxen, wafarin, papaverine, thioabenazole, miconazole, cinarizin, doxorubicin, omeprazole, colecalciferol, melphalan, nifedipine, digoxin, benzoic acid tryptophan, tyrosine, phenylalanine, azthreonam, ibuprofen, penoxymethylpenicillin, thalidomide, methyl testosterone, prochlorperazine, hydrocortisone, dideoxypurine nucleoside, vitamin $D_2$, sulfonamide, sulfonyl urea, para-aminobenzoic acid, melatonin, benzyl penicillin, chlorambucil, diazepine, digitoxin, hydrocortisone butyrate, metronidazole benzoate, tolbutamide, prostaglandin, fludrocortisone, griseofulvin, miconazole nitrate, leucotriene B4 inhibitor, propranolol, theophylline, flubiprofen, sodium benzoate, benzoic acid, riboflavin, benzodiazepine, phenobarbital, glyburide, sulphiazine, sulfaethylthiadiazole, sodium diclofenac, phenytoin, hioridazine hydrochloride, bropyrimine, hydrochlorothiazide, fluconazole and the like.

Poorly water soluble drugs include antibiotics, anti-inflammatory analgesics, anesthetics, hormones, drugs for hypertension, drugs for diabetes, drugs for hyperlipidemia, anti-virus agents, drugs for Parkinson's disease, drugs for Alzheimer's disease, anti-emetic agents, immunosuppressive drugs, drugs for ulcers, drugs for constipation, or anti-malaria agents in addition to the above listed drugs.

Preferably, drug containing micelle composition of the present invention comprises a poorly water soluble drug in the amount of 0.1 to 20.0 wt %, and 80.0 to 99.9 wt % of the polylactic acid derivatives. The polylactic acid derivatives may be administered orally or parentally in the form of micelles containing the poorly water soluble drugs.

Parental administration means injection of poorly water soluble drugs via blood vessel, subcutaneous fat, muscle, and the like, and more specifically injection via subcutaneous fat or muscle, after mixing the polylactic acid derivative with a poorly water soluble drug. Also, formulations for oral administration include tablets or capsules prepared by mixing the polylactic acid derivatives of the present invention with a poorly water soluble drug.

In addition, for parental administration, formulations that slowly form micelles in a body fluid of pH 6 to 7 may be prepared. For oral administration, a formulation which does not release the drug in the stomach at a pH of 1 to 2 but which releases the drug in the small intestine at a pH of 6 to 7 in the form of micelles which solubilize the drug, can be prepared.

The pharmaceutical composition comprising a poorly water soluble drug according to the present invention is transferred into the small intestine via the stomach when orally administered. If the pH of the stomach is lower than that of the small intestine, the polylactic acid derivatives contained in the pharmaceutical composition according to the present invention, maintain the form of a tablet or capsule at a low pH, and therefore the drug is not released. However, if the pharmaceutical composition is transferred into the small intestine at a pH of 6 to 7, the composition is slowly solubilized in the form of micelles containing the drug, and the drug is released and absorbed in the small intestine. This property has an advantage in that a drug which is unstable at a low pH may have improved stability by preventing its release at a low pH, and furthermore that a drug, such as an anti-inflammatory analgesic agent, etc. which is precipitated in solution at a pH of 1 to 2 and thus, has adverse effects such as causing stomach ulcers, etc., is not released in the stomach but in the small intestine where the pH is 6 to 7 which reduces adverse effects and improves its pharmacological effects.

The present invention also relates to a preparation method of micelles containing a poorly water soluble drug by using polylactic acid derivatives.

The polylactic acid derivatives and poorly water soluble drugs are dissolved in acetone, ethyl acetate, acetonitrile, dichloromethane, ethanol, methanol, chloroform, or acetic acid, the organic solvent is removed, and a homogeneous mixture of the polylactic acid derivative and poorly water soluble drug is prepared. Distilled water is added and the pH of the aqueous solution is adjusted to 4 to 8, and thereby the micelles containing the drugs are automatically formed. The micelle solution containing the poorly water soluble drugs is then lyophilized.

Also, to prepare oral formulations, the polylactic acid derivatives and poorly water soluble drugs are dissolved in an organic solvent, the organic solvent is removed, and the mixture of polylactic acid derivative and poorly water soluble drug is mixed with oral excipients to produce tablets, or filled into capsules to produce a capsule formulation.

According to the Examples of the present invention, as a result of the solubilization tests for paclitaxel and cyclosporine, it is shown that the micelle sizes are from 14 to 35 nm, and the drug solubility should be 10 to 25 mg/ml to ensure solubilization of the drugs.

The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

Examples 1-12

Synthesis of Polylactic Acid Derivatives

The was prepared by polymerization of a 2-hydroxycarboxylic acid derivative, in the absence of a catalyst, at an elevated temperature (100 to 200° C.) and under a reduced pressure (100 to 0.1 mmHg) for 6 to 24 hours, followed by purification.

Example 1

Synthesis 1 of D,L-Polylactic Acid (PLA-COOH)

D, L-lactic acid (100 g) was introduced into a 250 ml three-neck round-bottomed flask. The to flask was equipped with a stirrer. The reaction was performed for 1 hour while the flask was heated in an oil bath at 80° C. and its pressure was reduced to 25 mmHg with a vacuum aspirator to remove excessive moisture. The reaction was then performed for 6 hours at an elevated temperature of 150° C. under a reduced pressure of 25 mmHg, and then, the reaction was stopped. To the product formed was added 1 liter of distilled water to precipitate the polymer. The precipitated polymer was added to distilled water removing the oligomer with low molecular weight which is soluble in an aqueous solution at a pH of 4 or less. Then, the precipitated polymer was added to 1 liter of distilled water, the pH of the aqueous solution was adjusted to 6 to 8 by adding sodium bicarbonate portionwise, thereby dissolving the polymer. At this time, the water-insoluble polymer was separated and removed by centrifugation or filtration. The pH of the aqueous solution was adjusted to 2 by adding 1 N hydrochloric acid solution dropwise thereto to precipitate the polymer in the aqueous solution. The precipitated polymer was washed twice with distilled water, isolated and dried under reduced pressure obtaining a non-crystalline polymer (59 g of D,L-polylactic acid, yield: 59%). The number average molecular weight of the polymer was 540 daltons by $^1$H-NMR spectrum (FIG. 1).

Example 2

Synthesis 2 of D,L-Polylactic Acid (PLA-COOH)

D,L-polylactic acid was obtained according to the same procedure as in Example 1 except that the reaction was performed for 12 hours at an elevated temperature of 160° C. under a reduced pressure of 10 mmHg obtaining 66 g (yield: 66%) of D,L-polylactic acid having a number average molecular weight of 1,140 daltons.

Example 3

Synthesis 3 of D,L-Polylactic Acid (PLA-COOH)

D,L-polylactic acid was obtained according to the same procedure as in Example 1 except that the reaction was performed for 24 hours at an elevated temperature of 160° C. under a reduced pressure of 10 mmHg obtaining 71 g (yield: 71%) of D,L-polylactic acid having a number average molecular weight of 1,550 daltons.

Example 4

Synthesis 4 of D,L-Polylactic Acid (PLA-COOH)

D,L-polylactic acid was obtained according to the same procedure as in Example 1 except that the reaction was performed for 24 hours at an elevated temperature of 160° C. under a reduced pressure of 5 mmHg obtaining 75 g (yield: 75%) of D,L-polylactic acid having a number average molecular weight of 2,100 daltons.

The D,L-polylactic acids synthesized from the above Examples 1 to 4 are shown in the following Table 1.

TABLE 1

| Example | Temperature (° C.) | Time (hours) | Pressure (mmHg) | Mn (Daltons) | Yield (%) |
|---|---|---|---|---|---|
| 1 | 150 | 6 | 25 | 540 | 59 |
| 2 | 160 | 12 | 10 | 1,140 | 66 |
| 3 | 160 | 24 | 10 | 1,550 | 71 |
| 4 | 160 | 24 | 5 | 2,100 | 75 |

*Yield = (Obtained polymer/Used monomer) × 100

Example 5

Synthesis 1 of the Copolymer of D,L-Lactic Acid and Glycolic Acid (PLGA-COOH)

D,L-lactic acid (55 g, 0.6 moles) and glycolic acid (45 g, 0.6 moles) were introduced together into a 250 ml three-neck round-bottomed flask. The same procedure as in the above Example 1 was carried out except that the reaction was performed for 12 hours at an elevated temperature of 150° C. and under a reduced pressure of 10 mmHg obtaining 63 g (yield: 63%) of a copolymer of D,L-lactic acid and glycolic acid (PLGA-COOH) having a number average molecular weight of 920 daltons. The molar ratio of D,L-lactic acid/glycolic acid in the obtained product was 52/48.

Example 6

Synthesis 2 of the Copolymer of D,L-Lactic Acid and Glycolic Acid (PLGA-COOH)

D,L-lactic acid (73 g, 0.8 moles) and glycolic acid (27 g, 0.35 moles) were introduced together into a 250 ml three-neck round-bottomed flask. The same procedure as in the above Example 1 was carried out except that the reaction was performed for 12 hours at an elevated temperature of 160° C., under a reduced pressure of 10 mmHg obtaining 65 g (yield: 65%) of a copolymer of D,L-lactic acid and glycolic acid (PLGA-COOH) having a number average molecular weight of 1,040 daltons. The molar ratio of D,L-lactic acid/glycolic acid in the obtained product was 67/33.

Example 7

Synthesis 3 of the Copolymer of D,L-Lactic Acid and Glycolic Acid (PLGA-COOH)

D,L-lactic acid (91 g, 1.0 mole) and glycolic acid (9 g, 0.12 moles) were introduced together into a 250 ml three-neck round-bottomed flask. The same procedure as in the above Example 1 was carried out except that the reaction was performed for 12 hours at an elevated temperature of 160° C. and under a reduced pressure of 10 mmHg obtaining 68 g (yield: 68%) of a copolymer of D,L-lactic acid and glycolic acid (PLGA-COOH) having a number average molecular weight of 1,180 daltons. The molar ratio of D,L-lactic acid/glycolic acid in the obtained product was 91/9.

Example 8

Synthesis 4 of the Copolymer of D,L-Lactic Acid and Glycolic Acid (PLGA-COOH)

D,L-lactic acid (73 g, 0.8 moles) and glycolic acid (27 g, 0.35 moles) were introduced together into a 250 ml three-neck round-bottomed flask. The same procedure as in the above Example 1 was carried out except that the reaction was performed for 12 hours at an elevated temperature of 180° C. and under a reduced pressure of 5 mmHg obtaining 73 g (yield: 73%) of a copolymer of D,L-lactic acid and glycolic acid (PLGA-COOH) having a number average molecular weight of 1,650 daltons. The molar ratio of D,L-lactic acid/glycolic acid in the obtained product was 71/29.

The copolymers synthesized from the above Examples 5 to 8 are shown in Table 2.

TABLE 2

| Example | Molar ratio of lactic acid and glycolic acid | | Reaction temperature (° C.) | Reaction time (hrs) | Pressure (mmHg) | Mn (Daltons) | Yield (%) |
|---|---|---|---|---|---|---|---|
| | Reactant | Product | | | | | |
| 5 | 50/50 | 52/48 | 150 | 12 | 10 | 920 | 63 |
| 6 | 70/30 | 67/33 | 160 | 12 | 10 | 1,040 | 65 |
| 7 | 90/10 | 91/9 | 160 | 12 | 10 | 1,180 | 68 |
| 8 | 70/30 | 71/29 | 180 | 24 | 5 | 1,650 | 73 |

Example 9

Synthesis of the Copolymer of D,L-Lactic Acid and Mandelic Acid (PLMA-COOH)

D,L-lactic acid (75 g) and D,L-mandelic acid (25 g) were introduced together into a 250 ml three-neck round-bottomed flask. The flask was equipped with a stirrer. The reaction was performed for 1 hour while the flask was heated in an oil bath at 80° C., its pressure was reduced to 25 mmHg with a vacuum aspirator to remove excessive moisture. The same procedure as in the above Example 1 was carried out except that the reaction was performed for 12 hours at an elevated temperature of 180° C. and under a reduced pressure of 10 to 20 mmHg obtaining 54 g (yield: 54%) of a copolymer of D,L-lactic acid and mandelic acid having a number average molecular weight of 1,750 Daltons. The molar ratio of D,L-lactic acid/mandelic acid in the obtained product was 85/15.

Example 10

Synthesis of an Acetoxy D,L-Polylactic Acid Derivative (AcO-PLA-COOH)

50 g of D,L-polylactic acid (Mn: 1,140' daltons) synthesized from the above Example 2 and 20 ml of acetyl chloride were introduced together into a 250 ml round-bottomed flask. The flask was equipped with a condenser, and the reaction mixture was refluxed under nitrogen flow for 4 hours. Excessive acetyl chloride was removed by distillation, and then, the reaction product was added to a mixture of ice and water. The whole mixture was slowly stirred to precipitate the polymer. The precipitated polymer was separated and washed twice with distilled water, and then, dissolved in anhydrous acetone. Anhydrous magnesium sulfate was added thereto to remove excess moisture. The product obtained was filtered to remove the magnesium sulfate. The acetone was removed using a vacuum evaporator to obtain highly viscous liquid acetoxy D,L-polylactic acid (46 g, yield: 92%). By $^1$H-NMR, the acetoxy group was identified as a single peak of 2.02 ppm.

Example 11

Synthesis of a Benzoyloxy D,L-Polylactic Acid Derivative (BenzoylO-PLA-COOH)

The same procedure as in the above Example 10 was carried out except that benzoyl chloride was added instead of chloracetic acid obtaining 47 g (yield: 94%) of benzoyloxy D,L-polylactic acid.

Example 12

Synthesis of a Palmitoyloxy D,L-Polylactic Acid Derivative (PalmO-PLA-COOH)

20 g of D,L-polylactic acid (Mn: 1,140 daltons) synthesized from the above Example 2 was introduced into a 250 ml round-bottomed flask. The reactant was completely dehydrated under vacuum in an oil bath of 120° C. The oil bath was cooled to 50° C. and 50 ml of acetone was added thereto to completely dissolve the polymer. Thereto was added 5 ml of palmitoyl chloride, and the reaction was performed for 10 hours at a temperature of 50° C. under nitrogen atmosphere. The reaction product was washed with an excess amount of hexane to remove residual reactant. Hexane was removed by distillation. Then, the reaction product was dissolved in acetone and the solution was added to a mixture of ice and water. The whole mixture was slowly stirred to precipitate the polymer. The polymer was separated and washed twice with distilled water, and then, dissolved in anhydrous acetone. Anhydrous magnesium sulfate was added thereto to remove excess moisture. The product obtained was filtered to remove the magnesium sulfate, the acetone was removed with a vacuum evaporator, obtaining a palmitoyloxy D,L-polylactic acid derivative (19.1 g, yield: 96%). By $^1$H-NMR, the palmitoyl group was identified as peaks of 0.88, 1.3 and 2.38 ppm.

Examples 13 to 22

Synthesis of the Carboxylate Salts of Polylactic Acid Derivatives

The polylactic acid derivatives synthesized from the above Examples 1 to 12 were dissolved in acetone or its aqueous solution, and then, reacted with sodium bicarbonate, sodium carbonate, potassium bicarbonate, or potassium carbonate, or their aqueous solutions, to prepare their carboxylate salts.

Example 13

Synthesis 1 of the Sodium Salt of Polylactic Acid (PLA-COONa)

Figure 2:
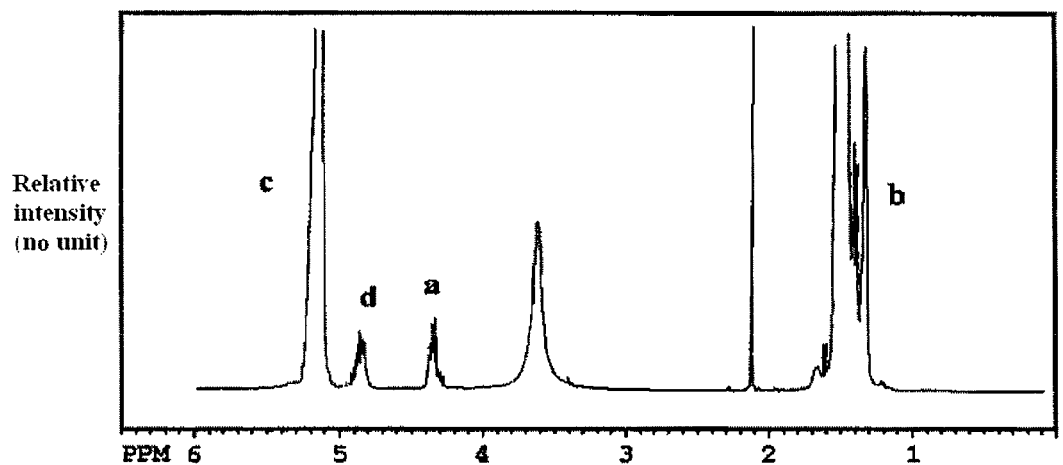
FIG. 2 is a graph showing an $^1$H-NMR spectrum of the sodium salt of a D,L-polylactic acid of the present invention.
Figure 2:
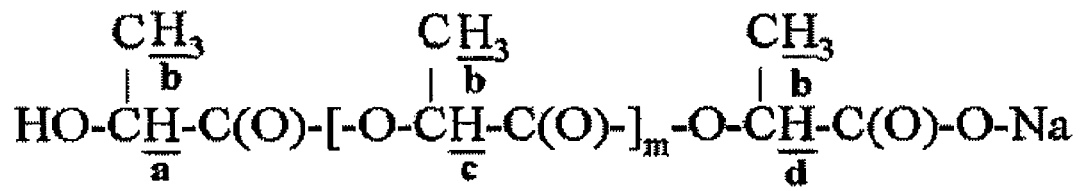

D,L-polylactic acid (Mn: 540 daltons) synthesized from the above Example 1 was dissolved in acetone. The solution was introduced into a round-bottomed flask and the flask was equipped with a stirrer. The solution was slowly stirred at room temperatures and sodium bicarbonate solution (1 N) was slowly added thereto to neutralize it, until a pH of 7 was reached. A small amount of acetone solution was taken and diluted in a large amount of distilled water to measure the pH of the solution. Anhydrous magnesium sulfate was added thereto and excess moisture was removed therefrom. The mixture obtained was filtered and acetone was evaporated with a solvent evaporator obtaining white solid. The solid was dissolved in anhydrous acetone and the solution was filtered to remove the insoluble residue in anhydrous acetone. Acetone was evaporated obtaining sodium salt of D,L-polylactic acid (yield: 96%) as a white solid. As shown in FIG. 2, a hydrogen peak adjacent to the carboxylic acid group was observed at 4.88 ppm by $^1$H-NMR, and the polymer formed dissolved in water had a pH of 6.5 to 7.5.

Example 14

Synthesis 2 of the Sodium Salt of Polylactic Acid (PLA-COONa)

The sodium salt of polylactic acid (yield: 95%) was synthesized according to the same procedure as in the above Example 13 except that D,L-polylactic acid (Mn: 1,140 daltons) synthesized from the above Example 2 and an aqueous solution of sodium carbonate were used.

Example 15

Synthesis of the Sodium Salt of Acetoxy-D,L-Polylactic Acid (AcO-PLA-COONa)

The sodium salt of acetoxy-D,L-polylactic acid (yield: 95%) was synthesized according to the same procedure as in the above Example 13 except that acetoxy-D,L-polylactic acid (Mn: 1,140 daltons) synthesized from the above Example 10 and an aqueous solution of sodium carbonate were used.

Example 16

Synthesis of the Sodium Salt of Palmitoyloxy D,L-Polylactic Acid (PalmO-PLA-COONa)

The palmitoyloxy D,L-polylactic acid (Mn: 1,140 daltons) synthesized from the above Example 12 was completely dissolved in an aqueous solution of acetone (28.6 v/v %). The solution was introduced into a round-bottomed flask and the flask was equipped with a stirrer. The solution was slowly stirred at a room temperature, and then, an aqueous solution of sodium bicarbonate (1 N) was added thereto until the pH value is 7. Anhydrous magnesium sulfate was added thereto to remove excess moisture. The product obtained was filtered, and the acetone solvent was evaporated with a solvent evaporator obtaining a white solid. The solid was dissolved in anhydrous acetone and the solution was filtered to removing the insoluble residue in anhydrous acetone. Acetone was evaporated obtaining the sodium salt of palmitoyl D,L-polylactic acid as a white solid (yield: 96%).

Example 17

Synthesis of Potassium Salt of Polylactic Acid (PLA-COOK)

The potassium salt of polylactic acid (yield: 98%) was synthesized according to the same procedure as in the above Example 13 except that D,L-lactic acid (Mn: 1,550 daltons) synthesized from the above Example 3 and an aqueous solution of potassium bicarbonate were used.

Example 18

Synthesis 3 of Sodium Salt of Polylactic Acid (PLA-COONa)

The sodium salt of polylactic acid (yield: 95%) was synthesized according to the same procedure as in the above Example 13 except that D,L-lactic acid (Mn: 2,100 daltons) synthesized from the above Example 4 was used.

Example 19

Synthesis 1 of Sodium Salt of the Copolymer of D,L-Lactic Acid and Glycolic Acid (PLGA-COONa)

The sodium salt of a copolymer of D,L-lactic acid and glycolic acid (yield: 98%) was synthesized according to the same procedure as in the above Example 13 except that a copolymer of D,L-lactic acid and glycolic acid (Mn: 920 daltons) synthesized from the above Example 5 and an aqueous solution of sodium carbonate were used.

Example 20

Synthesis 2 of Sodium Salt of the Copolymer of D,L-Lactic Acid and Glycolic Acid (PLGA-COONa)

The sodium salt of a copolymer of D,L-lactic acid and glycolic acid (yield: 93%) was synthesized according to the same procedure as in the above Example 13 except that a copolymer of D,L-lactic acid and glycolic acid (Mn: 1,040 daltons) synthesized from the above Example 6 were used.

Example 21

Synthesis of Potassium Salt of the Copolymer of D,L-Lactic Acid and Glycolic Acid (PLGA-COOK)

The potassium salt of a copolymer of D,L-lactic acid and glycolic acid (yield: 92%) was synthesized according to the same procedure as in the above Example 13 except that a copolymer of D,L-lactic acid and glycolic acid (Mn: 1,180 daltons), synthesized from the above Example 7, and an aqueous solution of potassium carbonate were used.

Example 22

Synthesis 3 of the Sodium Salt of the Copolymer of D,L-Lactic Acid and Glycolic Acid (PLGA-COONa)

The sodium salt of a copolymer of D,L-lactic acid and glycolic acid (yield: 98%) was synthesized according to the same procedure as in the above Example 13 except that a copolymer of D,L-lactic acid and glycolic acid (Mn: 1,650 daltons) synthesized from the above Example 8 were used.

The carboxylate metal ion salts of the polylactic acid derivatives synthesized from the above Examples 13 to 22 are shown in the following Table 3.

TABLE 3

| Example | Reactant (MW) | Base | Product | Mn (Daltons) | Yield (%) |
|---|---|---|---|---|---|
| 13 | PLA-COOH (540) | NaHCO$_3$ | PLA-COONa | 540 | 96 |
| 14 | PLA-COOH (1,140) | Na$_2$CO$_3$ | PLA-COONa | 1,140 | 95 |
| 15 | AcO-PLA-COOH (1,140) | Na$_2$CO$_3$ | AcO-PLA-COONa | 1,140 | 95 |
| 16 | PalmO-PLA-COOH (1,140) | NaHCO$_3$ | PalmO-PLA-COONa | 1,140 | 96 |
| 17 | PLA-COOH (1,550) | KHCO$_3$ | PLA-COOK | 1,550 | 98 |
| 18 | PLA-COOH (2,100) | NaHCO$_3$ | PLA-COONa | 2,100 | 95 |
| 19 | PLGA-COOH (920) | Na$_2$CO$_3$ | PLGA-COONa | 920 | 98 |
| 20 | PLGA-COOH (1,040) | NaHCO$_3$ | PLGA-COONa | 1,040 | 93 |
| 21 | PLGA-COOH (1,180) | K$_2$CO$_3$ | PLGA-COOK | 1,180 | 92 |
| 22 | PLGA-COOH (1,650) | NaHCO$_3$ | PLGA-COONa | 1,650 | 98 |

Experimental Example 1

Micelle Formation Depending on pH

The sodium salt of D,L-polylactic acid (Mn: 1,000 daltons) was dissolved in an aqueous solution, and micelle formation was evaluated by adjusting the pH of the solution. The particle size of the formed micelles was measured using DLS (Dynamic Light Scattery, ZetaPlus, Brookhaven Instruments Corp.) The results are shown in FIG. 7 and Table 4.

TABLE 4

| pH | Micelle formation | Average particle size of micelle (nm) |
|---|---|---|
| 2 | X | — |
| 4 | O | 12 |
| 6 | O | 12 |

The polymer formed micelles in an aqueous solution of pH 4 or more, becoming a clear solution, but was precipitated at a pH of 4 or less.

Experimental Example 2

Micelle Formation Depending on M.W.

Each D,L-polylactic acid having a number average molecular weight of 200, 500, and 700 daltons were dissolved in distilled water, and their solubility and pH were measured. D,L-polylactic acid with a Mw of 200 Daltons formed a clear aqueous solution, but the polymer was precipitated in the solution of D,L-polylactic acid of 500 daltons or more. The pH of the above aqueous solution was 1-2. The pH of the aqueous solution was adjusted to 6.5 to 7.5 to completely dissolve the D,L-polylactic acid. The particle size of the micelle formed was measured using DLS (Dynamic Light Scattery, ZetaPlus, Brookhaven Instruments Corp.) The results are shown in Table 5.

TABLE 5

| Mn (Daltons) | Average particle size of micelle (nm) |
|---|---|
| 200 | Immeasurable |
| 500 | 9.2 |
| 700 | 12 |

Experimental Example 3

Micelle Formation Depending on Concentrations and Kinds of Polymers

The polylactic acid derivatives synthesized from the above Examples 1 to 22 were dissolved in distilled water. Then, it was confirmed whether micelles were formed, and the size of the formed micelles was measured. The polylactic acid derivatives from Examples to 12 were dissolved in distilled water, the pH was adjusted using sodium bicarbonate, etc., and those from Examples 13 to 22 were dissolved without adjusting the pH because they were inherently soluble in water. The pH of the solution, after dissolving the polylactic acid derivatives, was 6.5 to 7.5. The solubility of the polylactic acid derivative was measured the polymer was added to distilled water and the mixture was vigorously shaken for 30 seconds at intervals of 5 minutes. The polymer (1 g) was dissolved in 10 ml of distilled water and the aqueous solution was passed through a membrane filter with the pore size of 200 nm. The polymeric aqueous solution was clear and transparent. The polylactic acid derivative was confirmed to be readily soluble in water from the fact that the concentration of the polymer was unchanged after filtration.

In addition, the above polymer was dissolved in PBS (Phosphate Buffered Saline) with a pH of 7.4, and it was confirmed, using SEC (Size Exclusion Chromatography, Water 410 Differential Refractometer), whether micelles were formed or not. The mobile phase was PBS containing NaCl (6 g/ml) and the flow rate was 1 ml/min. Micelle formation depending on the concentrations and kinds of the polymers used is shown in FIG. 3 and the following Table 6.

TABLE 6

| Micelle formation depending on concentrations and kinds of polymers | | | |
|---|---|---|---|
| Conc. of polymer (mg/ml) | Area of micellized PLA-COONa (a) | Area of free PLA-COONa (b) | a/b |
| 6.25 | 60,107 | 132,913 | 0.45 |
| 12.5 | 154,690 | 266,794 | 0.58 |
| 25 | 355,459 | 508,965 | 0.70 |
| 50 | 797,774 | 947,810 | 0.84 |
| Conc. of polymer (mg/ml) | Area of micellized PalmO-PLA-COONa (a) | Area of free PalmO-PLA-COONa (b) | a/b |
| 6.25 | 1,735,374 | 91,192 | 19.03 |
| 12.5 | 3,773,480 | 157,852 | 23.91 |
| 25 | 7,836,980 | 267,143 | 29.34 |
| 50 | 16,600,792 | 537,877 | 30.86 |

As shown in FIG. 3, each peak of micellized polymer part (a) and dissolved polymer part (b) was shown in the spectrum. In addition, as shown in Table 6, as the concentration of the polymer was increased, the relative area of the peak showing the micellized polymer part was increased. From above results, it was confirmed that the content of the micelles formed was increased as the concentration of polymer was increased.

Furthermore, the particle size of the formed micelle was measured using DLS (Dynamic Light Scattery, ZetaPlus, Brookhaven Instruments Corp.) The results are shown in Table 7.

TABLE 7

Particle size of the formed micelle

| Example | Average particle size (nm) | Concentration of polymeric aqueous solution (mg/ml) |
|---|---|---|
| 13 | 10 | 10 |
| 14 | 12 | 10 |
| 15 | 15 | 10 |
| 16 | 21 | 10 |
| 17 | 15 | 10 |
| 18 | 21 | 10 |
| 19 | 12 | 10 |
| 20 | 13 | 10 |
| 21 | 15 | 10 |
| 22 | 18 | 10 |

As shown in Table 7, the average particle size of the formed micelle was 10 to 21 nm. The suitable sizes of polymeric micelles is 100 nm or less, which minimizes capture of the drug by the reticuloendothelial system (RES) in vivo due to the hydrophilic outer shell of the polymeric micelle, which enables systemic circulation for a long period of time. Suppression of excretion through the kidney is due to the high molecular weight. The micelle, in accordance with the present invention, not only has a suitable size for the above conditions but also has a wide range of applicability due to its increased stability because of its small size.

Experimental Example 4

Solubilization Test of Poorly Water-Soluble Drug

The sodium salt of a D,L-polylactic acid derivate, synthesized from the above examples, and paclitaxel were dissolved together in an organic solvent such as acetone, ethanol, ethyl acetate, acetonitrile, dichloromethane, or chloroform obtaining a clear solution. The organic solvent was removed from the solution with a vacuum evaporator obtaining a homogeneous mixture of the poorly water-soluble drug and the sodium salt of the D,L-polylactic acid derivate. This mixture was dissolved in an aqueous solution with a pH of 4-8. The formed poorly water-soluble drug-containing micelle aqueous solution was passed through a membrane filter with a pore size of 200 nm to remove the undissolved drug. Then, the drug concentration in the aqueous solution was quantitated by liquid chromatography. The results are shown in Table 8.

TABLE 8

| Polymer (MW) | Drug | Ratio of drug/ polymer (%) | Size of micelle (nm) | Solubility of drug (mg/ml) |
|---|---|---|---|---|
| PLA-COONa (1,140) | Paclitaxel | 5 | 14 | 25 |
| PLA-COONa (1,140) | Paclitaxel | 10 | 24 | 20 |
| PLA-COONa (1,140) | Paclitaxel | 15 | 30 | 15 |
| PLA-COOK (1,550) | Cyclosporine | 1 | 18 | 15 |
| PLGA-COONa (2,100) | Cyclosporine | 5 | 28 | 21 |
| PLGA-COONa (1,040) | Cyclosporine | 10 | 35 | 22 |
| PLGA-COONa (1,180) | Paclitaxel | 5 | 16 | 25 |
| PLGA-COOK (1,650) | Cyclosporine | 2 | 18 | 10 |
| PLGA-COONa (1,650) | Paclitaxel | 10 | 29 | 23 |
| PalmO-PLA-COONa (1,140) | Paclitaxel | 10 | 34 | 23 |

As shown above in Table 8, the polylactic acid derivatives of the present invention effectively solubilize poorly water-soluble drugs such as paclitaxel and cyclosporine. Palitaxel has a solubility of 0.01 mg/ml or less in water, but a large amount, i.e. 15 to 25 mg/ml, of paclitaxel can be solubilized in the form of micelles using the polylactic acid derivatives of the present invention, and so a large amount of drug can be administered into the body.

Figure 4:
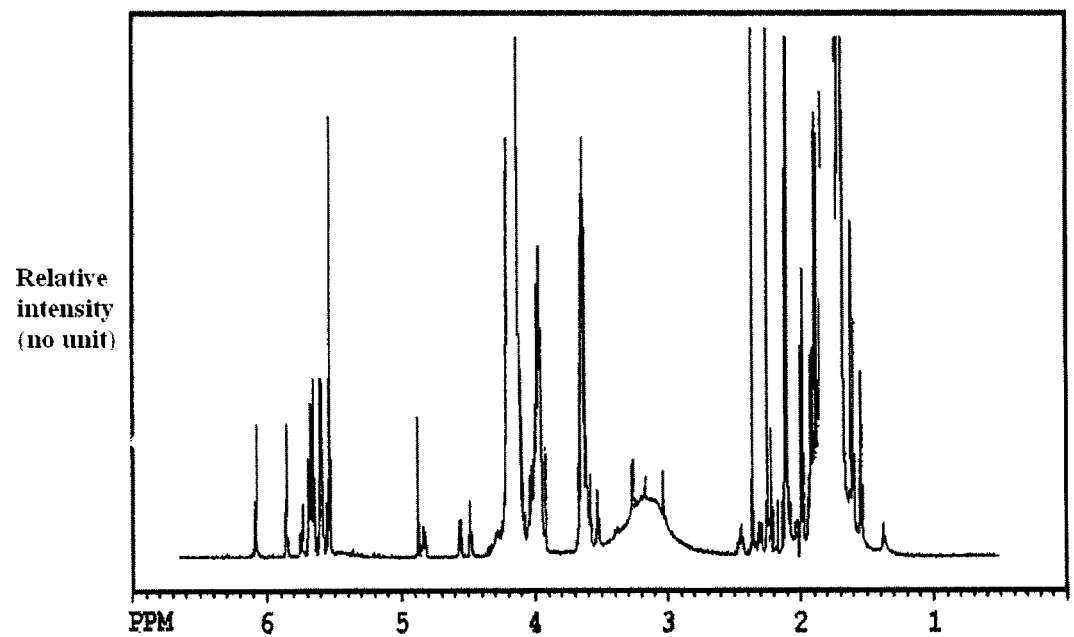
FIG. 4 is a graph showing an $^1$H-NMR spectrum of a mixture of the sodium salt of a D,L-polylactic acid and paclitaxel in $CDCl_3$ solvent.
Figure 5:
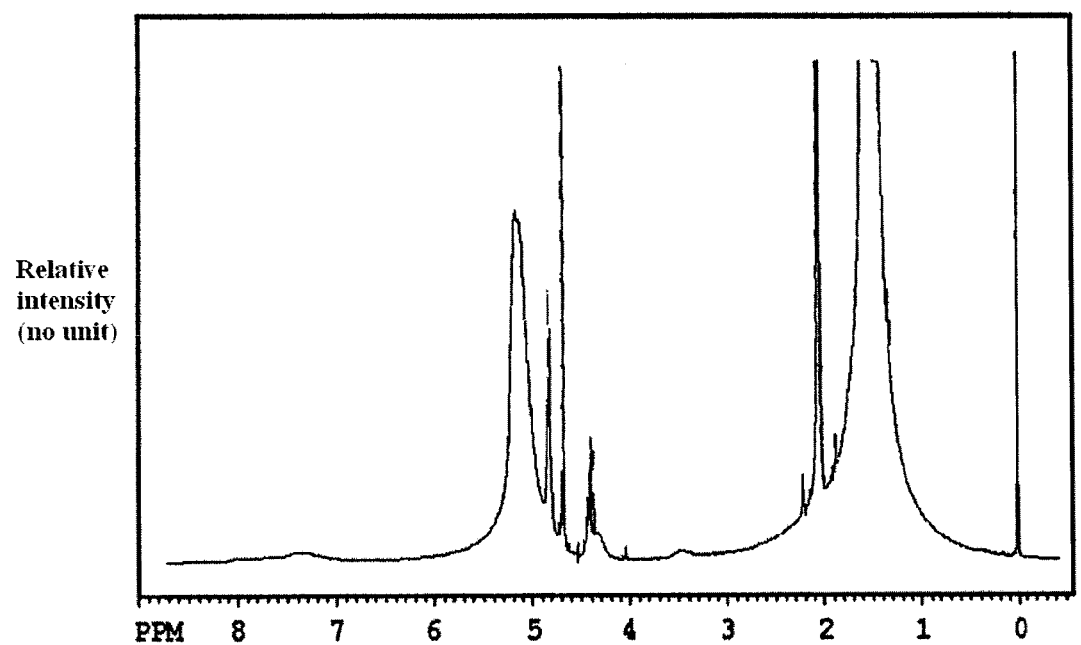
FIG. 5 is a graph showing an $^1$H-NMR spectrum of a mixture of the sodium salt of D,L-polylactic acid and paclitaxel in $D_2O$ solvent.

In addition, a mixture of paclitaxel and the sodium salt of D,L-polylactic acid derivates were dissolved in CDCl$_3$ and D$_2$O, and then subjected to $^1$H-NMR. The results are shown in FIGS. 4 and 5. As shown in FIG. 4, the polylactic acid could not form micelles because CDCl$_3$ was an organic solvent. Therefore, a characteristic peak of the benzoyloxy group of paclitaxel was shown at 7.0-8.2 ppm. However, as shown in FIG. 5, when it was dissolved in D$_2$O having little solubility for paclitaxel, paclitaxel was entrapped into the micelles of the polylactic acid derivative and solubilized. Therefore, no peak of the benzoyloxy group was shown at 7.0 to 8.2 ppm in the $^1$H-NMR spectrum. The above result was obtained because paclitaxel was surrounded by micelles of the polylactic acid derivative so forming a core, and so was not affected by the magnetic field of the NMR.

Experimental Example 5

Preparation and Evaluation of pH-Dependent Poorly Water-Soluble Drug-Containing Micelles 900 mg of the sodium salt of D,L-polylactic acid synthesized from the above Example 13 and 100 mg of cyclosporine were dissolved in 10 ml of acetone. Then, acetone was removed using a vacuum evaporator to obtain a homogeneous solid mixture of the sodium salt of D,L-polylactic acid derivates and cyclosporine. The solid was compressed with a press to prepare a disk with a diameter of 1 cm and a thickness of 2 mm. The cyclosporine-containing disk was added to 10 ml of hydrochloric acid solution at a pH of 2, and the cyclosporine concentration in the aqueous solution was measured at time intervals while incubating at 37° C. After 2 hours, sodium bicarbonate was added thereto and the pH of the aqueous solution was adjusted to 6.2, and then, the cyclosporine concentration in the aqueous solution was measured at time intervals while incubating under the same conditions. The results are shown in FIG. 6.

Figure 6:
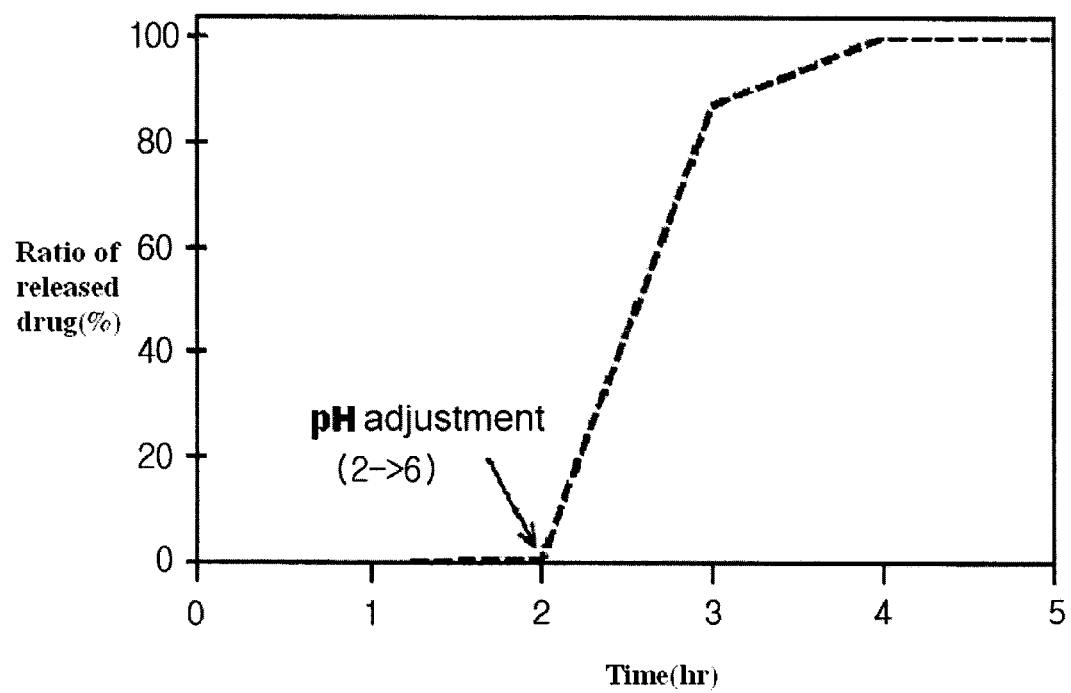
FIG. 6 is a graph showing the solubilization of cyclosporine depending on the pH.

As shown in FIG. 6, since the polylactic acid derivative was not solubilized at a pH of 2, the drug was not released from the discal solid. Thereafter, when the pH was changed from 2 to 6, the polylactic acid derivative was slowly solubilized while containing the drug in the form of micelles and the drug was gradually released into the aqueous phase. Furthermore, when the pH was adjusted to 6, about 80% of the drug was released within 1 hour, and 100% of the drug was released after 2 hours.

The above results show that, depending on the pH, the polylactic acid derivative can solubilize the drug by entrapping the drug within the micelle comprising the polylactic acid derivative, and that the degree of solubilization, with the lapse of time, after adjusting the pH can be determined. In the case of the oral administration of a formulation comprising a poorly water-soluble drug and the polylactic acid derivative, it is anticipated that the drug will not released in the stomach, and then, solubilized and absorbed in the small intestine.

It is to be understood that the above-described embodiments are only illustrative of the applications of the principles of the present invention. Numerous modifications and alternative embodiments can be derived without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth in the claims.

We claim:

1. A micellar composition comprising a di- or poly-lactic acid derivative in an aqueous solution with a pH of 4 or higher, said di- or poly-lactic acid derivative can be represented by formula (I):

$$RO\text{—}CHZ\text{-}[A]_n\text{-}[B]_m\text{-}COOM \quad (I)$$

wherein A is —COO—CHZ; B is —COO—CHY—, —COO—CH$_2$CH$_2$CH$_2$CH$_2$CH$_2$—, or —COO—CH$_2$CH$_2$OCH$_2$—; R is hydrogen, an acetyl, benzoyl, decanoyl, methyl, or ethyl group; Z and Y are hydrogen, methyl, or phenyl groups; M is sodium, potassium, or lithium; n is an integer from 5 to 30; and m is an integer from 0 to 20, and wherein the di- or poly-lactic acid derivative has a number average molecular weight of 500 to 2,000 Daltons.

2. The micellar composition according to claim 1, wherein the di- or poly-lactic acid derivative is a member selected from the group consisting of D,L-polylactic acid, a copolymer of D,L-lactic acid and mandelic acid, a copolymer of D,L-lactic acid and glycolic acid, a copolymer of D,L-lactic acid and caprolactone, and a copolymer of D,L-lactic acid and 1,4-dioxane-2-one.

3. The micellar composition according to claim 1, wherein M is sodium, or potassium.

4. The micellar composition according to claim 1, wherein the di- or poly-lactic acid derivative of formula (I) is made from a process comprising:
1) polycondensing monomers of a di- or poly-lactic acid derivative at an elevated temperature under a reduced pressure;
2) adding distilled water to the product of step 1 to precipitate the di- or poly-lactic acid derivative and thereby removing a low-molecular weight oligomer;
3) adding the di- or poly-lactic acid derivative to a neutral or alkaline aqueous solution to dissolve the di- or poly-lactic acid derivative;
4) isolating the di- or poly-lactic acid derivative from the solution of step 3; and
5) adding an alkali metal salt to the di- or poly-lactic acid derivative obtained in step 4.

5. The micellar composition according to claim 4, wherein isolating the di- or poly-lactic acid derivative in step 4 is conducted by adding acid to the aqueous solution of step 3 and adjusting pH to 1.5~2.5 to precipitate the di- or poly-lactic acid derivative.

6. The micellar composition according to claim 4, wherein isolation of the di- or poly-lactic acid derivative in step 4 is conducted by adding an organic solvent to the aqueous solution of step 3 to extract the di- or poly-lactic acid derivative.

7. The micellar composition according to claim 4, wherein the alkali metal salt in step 5 is selected from the group consisting of sodium bicarbonate, sodium carbonate, potassium bicarbonate, potassium carbonate and lithium carbonate.

8. The micellar composition according to claim 1, wherein R is an acetyl, benzoyl, decanoyl, methyl, or ethyl group and the di- or poly-lactic acid derivative is prepared from a process comprising the steps of:
1) polycondensing a monomer of a di- or poly-lactic acid derivative at an elevated temperature and under a reduced pressure;
2) adding distilled water to the product of step 1 to a precipitate a di- or poly-lactic acid derivative and thereby removing low-molecular weight oligomers;
3) adding the di- or poly-lactic acid derivative to a neutral or alkaline aqueous solution to dissolve the di- or poly-lactic acid derivative;
4) isolating the di- or poly-lactic acid derivative from the solution of step 3;
5) reacting the di- or poly-lactic acid derivative obtained in step 4 with acetic anhydride, acetyl chloride, benzoyl chloride, decanoyl chloride, methyl iodide, or ethyl iodide to substitute the di- or poly-lactic acid derivative; and
6) adding an alkali metal salt to the substituted di- or poly-lactic acid derivative.

9. The micellar composition according to the claim 8, wherein the step of isolating the di- or poly-lactic acid derivative in step 4 is conducted by adding acid to the aqueous solution of step 3 and adjusting pH to 1.5~2.5 to precipitate the di- or poly-lactic acid derivative.

10. The micellar composition according to the claim 8, wherein the step of isolating the di- or poly-lactic acid derivative in step 4 is conducted by adding an organic solvent to the aqueous solution of step 3 to extract the di- or poly-lactic acid derivative.

11. The micellar composition according to the claim 8, wherein the alkali metal salt in step 5 is selected from the group consisting of sodium bicarbonate, sodium carbonate, potassium bicarbonate, potassium carbonate, and lithium carbonate.

12. A pharmaceutical composition, wherein a poorly water soluble drug is entrapped in polymeric micelles of a micellar composition comprising a di- or poly-lactic acid derivative in an aqueous solution with a pH of 4 or higher, said di- or poly-lactic acid derivative can be represented by the following formula:

$$RO\text{—}CHZ\text{-}[A]_n\text{-}[B]_m\text{-}COOM$$

wherein A is —COO—CHZ; B is —COO—CHY—, —COO—CH$_2$CH$_2$CH$_2$CH$_2$CH$_2$— or —COO—CH$_2$CH$_2$OCH$_2$—; R is hydrogen, an acetyl, benzoyl, decanoyl, methyl, or ethyl group; Z and Y are hydrogen, methyl, or phenyl groups; M is sodium, potassium, or lithium; n is an integer from 1 to 30; and m is an integer from 0 to 20, and wherein the di- or poly-lactic acid derivative has a number average molecular weight of 500 to 2,000 Daltons.

13. The pharmaceutical composition according to claim 12, wherein the di- or poly-lactic acid derivative is a member selected from the group consisting of D,L-polylactic acid, a copolymer of D,L-lactic acid and mandelic acid, a copolymer of D,L-lactic acid and glycolic acid, a copolymer of D,L-lactic acid and caprolactone, and a copolymer of D,L-lactic acid and 1,4-dioxane-2-one.

14. The pharmaceutical composition according to claim 12, wherein M is sodium, or potassium.

15. The pharmaceutical composition according to claim 12, wherein the di- or poly-lactic acid derivative of said formula is made from a process comprising:
 1) polycondensing monomers of a di- or poly-lactic acid derivative at an elevated temperature under a reduced pressure;
 2) adding distilled water to the product of step 1 to precipitate the di- or poly-lactic acid derivative and thereby removing a low-molecular weight oligomer;
 3) adding the di- or poly-lactic acid derivative to a neutral or alkaline aqueous solution to dissolve the di- or poly-lactic acid derivative;
 4) isolating the di- or poly-lactic acid derivative from the solution of step 3; and
 5) adding an alkali metal salt to the di- or poly-lactic acid derivative obtained in step 4.

16. The pharmaceutical composition according to claim 15, wherein isolating the di- or poly-lactic acid derivative in step 4 is conducted by adding acid to the aqueous solution of step 3 and adjusting pH to 1.5~2.5 to precipitate the di- or poly-lactic acid derivative.

17. The pharmaceutical composition according to claim 15, wherein isolation of the di- or poly-lactic acid derivative in step 4 is conducted by adding an organic solvent to the aqueous solution of step 3 to extract the di- or poly-lactic acid derivative.

18. The pharmaceutical composition according to claim 15, wherein the alkali metal salt in step 5 is selected from the group consisting of sodium bicarbonate, sodium carbonate, potassium bicarbonate, potassium carbonate and lithium carbonate.

19. The pharmaceutical composition according to claim 12, wherein R is an acetyl, benzoyl, decanoyl, methyl, or ethyl group and the di- or poly-lactic acid derivative is prepared from a process comprising the steps of:
 1) polycondensing a monomer of a di- or poly-lactic acid derivative at an elevated temperature and under a reduced pressure;
 2) adding distilled water to the product of step 1 to a precipitate a di- or poly-lactic acid derivative and thereby removing low-molecular weight oligomers;
 3) adding the di- or poly-lactic acid derivative to a neutral or alkaline aqueous solution to dissolve the di- or poly-lactic acid derivative;
 4) isolating the di- or poly-lactic acid derivative from the solution of step 3;
 5) reacting the di- or poly-lactic acid derivative obtained in step 4 with acetic anhydride, acetyl chloride, benzoyl chloride, decanoyl chloride, methyl iodide, or ethyl iodide to substitute the di- or poly-lactic acid derivative; and
 6) adding an alkali metal salt to the substituted di- or poly-lactic acid derivative.

20. The pharmaceutical composition according to claim 19, wherein the step of isolating the di- or poly-lactic acid derivative in step 4 is conducted by adding acid to the aqueous solution of step 3 and adjusting pH to 1.5~2.5 to precipitate the di- or poly-lactic acid derivative.

21. The pharmaceutical composition according to claim 19, wherein the step of isolating the di- or poly-lactic acid derivative in step 4 is conducted by adding an organic solvent to the aqueous solution of step 3 to extract the di- or poly-lactic acid derivative.

22. The pharmaceutical composition according to claim 19, wherein the alkali metal salt in step 5 is selected from the group consisting of sodium bicarbonate, sodium carbonate, potassium bicarbonate, potassium carbonate, and lithium carbonate.

* * * * *